United States Patent

Guggenberger et al.

[11] Patent Number: 5,250,585
[45] Date of Patent: Oct. 5, 1993

[54] DENTAL MATERIAL IN POWDER FORM, PROCESS FOR ITS PREPARATION AND USE

[75] Inventors: Rainer Guggenberger, Seefeld; Klaus Ellrich, Wörthsee; Oswald Gasser, Seefeld, all of Fed. Rep. of Germany; John W. McLean, London, Great Britain; Owen Makinson, Wattle Park SA, Australia

[73] Assignee: ESPE Stiftung & Co. Produktions- und Vertriebs KG, Seefeld, Fed. Rep. of Germany

[21] Appl. No.: 466,363

[22] PCT Filed: Jul. 21, 1989

[86] PCT No.: PCT/EP89/00856

§ 371 Date: Mar. 21, 1990

§ 102(e) Date: Mar. 21, 1990

[87] PCT Pub. No.: WO90/00893

PCT Pub. Date: Feb. 8, 1990

[30] Foreign Application Priority Data

Jul. 22, 1988 [DE] Fed. Rep. of Germany ....... 3825027

[51] Int. Cl.$^5$ .......................... A61K 6/08; C08K 3/08
[52] U.S. Cl. .................... 523/116; 523/118; 524/432; 524/441; 524/408; 524/439; 524/440; 524/443
[58] Field of Search ................ 523/116, 118; 524/440, 524/443, 439, 441, 432, 408

[56] References Cited

U.S. PATENT DOCUMENTS

| | | | |
|---|---|---|---|
| 3,205,566 | 9/1965 | Breton | 29/182.5 |
| 4,209,434 | 6/1980 | Wilson et al. | |
| 4,527,979 | 7/1985 | McLean et al. | 433/228 |
| 4,569,954 | 2/1986 | Wilson et al. | |
| 4,814,362 | 3/1989 | Billington et al. | |
| 4,872,936 | 10/1989 | Engelbrecht | |

FOREIGN PATENT DOCUMENTS

| | | |
|---|---|---|
| 0219058 | 10/1986 | European Pat. Off. |
| 386338 | 12/1923 | Fed. Rep. of Germany |
| 584720 | 9/1933 | Fed. Rep. of Germany |
| 1458461 | 11/1973 | Fed. Rep. of Germany |
| 3042008 | 6/1982 | Fed. Rep. of Germany |
| 3248357 | 12/1983 | Fed. Rep. of Germany |
| 3628997 | 1/1989 | Fed. Rep. of Germany |
| 558112 | 12/1943 | United Kingdom |
| 1316129 | 5/1973 | United Kingdom |
| 2028855 | 3/1980 | United Kingdom |

OTHER PUBLICATIONS

Marxkors/Mieners, "Taschenbuch der zahnarztlichen Werkstoffkunde".
Pulvermetallurgie, p. 575.
Chem. Abs. 103, 1985.

Primary Examiner—Paul R. Michl
Assistant Examiner—LaVonda DeWitt
Attorney, Agent, or Firm—Birch, Stewart, Kolasch & Birch

[57] ABSTRACT

A dental material in powder form and being based on
(a) aluminum fluorosilicate glass,
(b) base metals suitable for dental use, or alloys of these with each other, and optionally
(c) dry polycarboxylic acid and/or
(d) a chelating agent, which contains at least some of constituent (a) as a sintered mixture with constituent (b).

8 Claims, No Drawings

DENTAL MATERIAL IN POWDER FORM, PROCESS FOR ITS PREPARATION AND USE

The invention relates to a powder-form dental material according to the preamble of claim 1, its preparation and use.

Glass-ionomer cements which are the reaction product of a calcium-aluminum-fluorosilicate-glass powder and/or a strontium-aluminum-fluorosilicate glass, a water-soluble polycarboxylic acid and water, have the advantage compared with other dental materials used for filling purposes (e.g. composite-plastic fillings, amalgam) that they are physiologically very well tolerated and enter into a chemical compound with the tooth-substance which results in a perfect marginal seal.

Glass-ionomer cement powders containing metal are known from GB-A-2 028 855. This material, however, is a simple mixture of cement powder and metal powder which is not subjected to any thermal treatment.

A powder-form dental material is known from DE-A-32 48 357 which consists of a sintered mixture of calcium-aluminum-fluorosilicate-glass and the noble metals commonly used for dental purposes or their alloys with up to 40% by weight of base metals. This sintered dental material has a markedly higher wear resistance than the glass-ionomer cements of unsintered dental material.

The aim of the invention is the preparation of a sintered, metal-containing glass-ionomer cement powder which can be prepared without using expensive noble metals at a quality comparable with the material in DE-A-32 48 357.

This aim is achieved according to the invention by preparing a powder-form dental material according to the preamble of claim 1, which contains at least some of constituent (a) as a sintered mixture with constituent (b).

The new powder-form dental material is prepared according to the invention by the process in claim 2 or 3. The sintered product obtained can optionally be mixed with (1) unsintered aluminum fluorosilicate glass and/or (2) with dry polycarboxylic acid and/or (3) with a chelating agent, each in powder form.

For use, the powder-form dental material according to the invention is mixed in case (1) with aqueous polycarboxylic acid solution, which optionally contains a chelating agent, in case (2) with water, optionally containing a chelating agent, e.g. a tartaric acid solution, and in case (3) with aqueous polycarboxylic acid solution or with water, to form a tooth-filling material which is distinguished by its high wear resistance and which is therefore also suitable for modelling edges and corners in the molar region. The cement prepared from the dental material according to the invention adheres thereby to the tooth-substance and has good physiological tolerability.

In addition to the glass powders containing calcium, magnesium and lanthanum mentioned in DE-A-20 61 513 and DE-A-32 48 357 and the glass powders containing strontium in EP-A-241 277, glass powders with other cations can also be used. Calcium- and/or strontium-fluorosilicate-glasses are preferably used, and thus the aluminum-fluorosilicate-glass powder can have the following constituents in addition to oxygen:

| Constituent | Calculated as | % by wt. |
| --- | --- | --- |
| Si | $SiO_2$ | 20–60 |
| Al | $Al_2O_3$ | 10–50 |
| Ca | CaO | 0–40 |
| Sr | SrO | 0–40 |
| F | F | 1–40 |
| Na | $Na_2O$ | 0–10 |
| P | $P_2O_5$ | 0–10 | in which at least 1% by weight of CaO and/or SrO must be included and in total 0–20% by weight, calculated as oxides, of B, Bi, Zn, Mg, Sn, Ti, Zr, La or other trivalent lanthanoids, K, W, Ge and further additives which do not disadvantageously affect the properties and are physiologically harmless. The glasses can be made x-ray visible by adding 10–20% by weight of $La_2O_3$.

The powder particles advantageously consist of:

| | |
| --- | --- |
| Si as $SiO_2$ | 25–50% by weight |
| Al as $Al_2O_3$ | 10–40% by weight |
| Ca as CaO | 0–35% by weight |
| Sr as SrO | 0–35% by weight |
| F | 5–30% by weight |
| Na as $Na_2O$ | 0–8% by weight |
| P as $P_2O_5$ | 1–10% by weight | in which at least 10% by weight of Ca (calculated as CaO) and/or Sr (calculated as SrO) must be contained and 0–10% by weight of $B_2O_3$, $Bi_2O_3$, ZnO, MgO, $SnO_2$, $TiO_2$, ZrO, $La_2O_3$ or other oxides of trivalent lanthanoids, $K_2O$, $WO_3$, $GeO_2$ and further additives which do not disadvantageously affect the properties and are physiologically harmless.

Particularly preferred powders contain

| | |
| --- | --- |
| Si as $SiO_2$ | 25–45% by weight |
| Al as $Al_2O_3$ | 20–40% by weight |
| Ca as CaO | 10–30% by weight |
| F | 10–30% by weight |
| Na as $Na_2O$ | 1–8% by weight |
| P as $P_2O_5$ | 1–10% by weight. |

Examples of the compounds preferably used are listed in Table I below:

TABLE I

| | % by weight | | | |
| --- | --- | --- | --- | --- |
| | A | B | C | D |
| Si as $SiO_2$ | 35.0 | 27.6 | 29.0 | 45.4 |
| Al as $Al_2O_3$ | 30.4 | 26.0 | 25.1 | 35.0 |
| Ca as CaO | 14.9 | 28.8 | 24.6 | 10.1 |
| F | 17.7 | 17.0 | 23.0 | 10.4 |
| Na as $Na_2O$ | 2.7 | 2.1 | 2.2 | 6.9 |
| P as $P_2O_5$ | 6.9 | 8.3 | 5.8 | 2.4 |

The glass powder particles used according to the invention can be made poor in calcium or strontium at the surface, as described in the case of calcium in EP-A-23 013. These powders can be used in particular as an admixture for the ground, metal-containing sintered product.

The glass powders used according to the invention have an average particle size (weight average) of at least 1 μm and preferably at least 3 μm. The average particle size (weight average) is 1–20 μm preferably 3–15 μm and particularly preferred 3–10 μm. The particles have a maximum size of 150 μm, preferably 100

μm, particularly 60 μm. For use as a dental fixing cement, the maximum particle size is 25 μm, preferably 20 μm. To obtain good mechanical properties, it is, in the usual way, favourable to have not too narrow a particle size distribution, such as obtained, for example, by the usual grinding and screening off of the coarse parts.

The glass powders are obtained in the usual manner by melting together the starting components at temperatures above 950° C., quenching and grinding.

All the metals which are solid at room temperature, and which are practically nonreactive with water or with atmospheric oxygen at ambient temperature and are physiologically tolerable, can be considered for use as the metal powders. The following metals in particular can be mentioned: tin, titanium, tantalum, germanium, niobium, aluminum and zinc. Tin, niobium, titanium and tantalum are particularly preferred. The most particularly preferred is tin. Alloys of these metals with each other can, however, also be considered for the use according to the invention.

The average particle size (weight average) of the metal powder component (b) is at least 0.5 μm, preferably at least 1 μm and particularly preferred at least 3 μm. The weight average of the particle size distribution is preferably between 0.5 and 20 μm, particularly between 1 and 10 μm. The maximum particle size of the metal powders should not exceed 60 μm, preferably 40 μm and most particularly 10 μm. Preferably, at least 90% of the particles of the metal powder component (b) have a particle size of less than 32 μm, particularly preferred of less than 10 μm.

The powder-form dental material according to the invention can also contain dry polycarboxylic acid; and as such the polycarboxylic acids known for the preparation of glass-ionomer cement powder, e.g. polymaleic acid, polyacrylic acid and mixtures thereof, or copolymers, particularly maleic acid/acrylic acid copolymers and/or acrylic acid/itaconic acid copolymers, can be used.

The dental material according to the invention can in addition contain a chelating agent (cf. DE-A-23 19 715). Tartaric acid is preferably used as the chelating agent.

In order to carry out the process according to the invention, the powder-form glass component and the powder-form metal component are first mixed together. The proportion of metal component to the total mixture can be 20-80 and preferably 40-60% by volume.

This mixture can be sintered directly—optionally under protective gas or in a vacuum; the sintering temperatures are >150° C., preferably >500° C. The mixture can also, however, first be moulded into formed bodies, which are then sintered—optionally under protective gas or in vacuum. The mixture or the formed bodies are preferably sintered under pressure—optionally under protective gas or in vacuum, particularly above 50 MPa. Mixtures or formed bodies which contain the low-melting metals tin and zinc are in particular sintered at pressures above 50 MPa. For this purpose, the mixtures or formed bodies and the mould are first pre-heated to the desired temperature and then the pressure is applied—optionally under protective gas or in a vacuum. In this way, even sinter times of a few minutes in the mould are sufficient to produce sintered products. Combinations of the methods given are also possible.

The sintered product obtained is finely ground and then screened off to the desired particle size. The object here is to obtain the same particle sizes as were described for the aluminum fluorosilicate-glass powder used.

To adjust the reactivity, the powder thus obtained can be mixed with the unsintered aluminum-fluorosilicate-glass described above. Additions of 10-50% by volume of unsintered glass powder—referred to the sintered product—are suitable here. In particular, powders poor in calcium or strontium at the surface can also be used here (cf. European Patent Specification 23 013).

The ground sintered product, or a mixture thereof with unsintered glass powder, can also be mixed with dry, finely particulate polycarboxylic acid in the weight ratio of 1:1 to 5:1.

It can also be advantageous to add pigments to improve the colouring. The colour can be further improved by thermally treating the ground sintered product again, optionally after adding a pigment. This is advantageously carried out under protective gas or in vacuum.

A chelating agent in powder form can also be added to one of these mixtures.

The powder-form dental materials according to the invention are used in the usual manner for glass-ionomer cement powders. If the dental material according to the invention does not contain dry polycarboxylic acid, it is mixed with an aqueous polycarboxylic acid solution in the weight ratio of 2:1 to 10:1, preferably 4:1 to 8:1, in which a chelating agent, e.g. tartaric acid, is optionally dissolved. The same polycarboxylic acids are suitable in the form of their aqueous solution as can be mixed in finely particulate dry form with the metal-containing powder according to the invention. If the dental material according to the invention already contains dry polycarboxylic acid, the dental material is mixed into a cement-like consistency with water, optionally with the addition of a chelating agent.

Surprisingly, cements are obtained with the dental materials according to the invention which have good corrosion resistance under the conditions in the mouth. Generally, the base metals used in the materials according to the invention—particularly tin—cannot be exposed unprotected in the mouth environment without severe instances of corrosion occurring in a short time.

When the low-melting metals tin and zinc are used, it is in addition surprising that the mixtures of glass powder and metal powder can be sintered at temperatures above the melting point of these metals without the glass powder separating from the (fused) metal powder. Instead a solid sintered body with an evenly distributed metal content is obtained after sintering at these temperatures. Even at temperatures far below the softening point of the glass (superficial softening identifiable at the earliest from approx. 600° C.), a solid metal/glass sintered product is obtained.

EXAMPLE 1

Sintered Powder Containing Tin 17.5 parts by weight of a calcium-aluminum-fluorosilicate-glass powder of composition B in Table I (average particle size 6 μm) are homogeneously mixed with 82.5 parts by weight of a finely particulate tin powder (all particles 42 μm).

The mixture is pre-heated to 200° C. and shaped in a mould, which has also been pre-heated to 200° C., for 3 minutes at a pressure of 80 MPa into cylindrical mouldings which have a diameter of 40 mm and a height of 5 mm.

The sintered product obtained is finely ground and screened to <63 μm.

96 parts by weight of this sintered powder are homogeneously mixed with 4 parts by weight of titanium dioxide and thermally treated further for 1 hour at 500° C. in a vacuum.

64.5 parts by weight of the metal-containing sintered product are mixed with 35.5 parts by weight of the unsintered calcium-aluminum-fluorosilicate-glass powder described above, which however was impoverished at the surface by treatment with 0.1% hydrochloric acid, as described in European Patent Specification 23 013.

The dental material obtained is mixed in the weight ratio 4.5:1 with a solution of 37 g of a copolymer (1:1) of acrylic acid and maleic acid, 9 g of tartaric acid and 54 g of water.

The cement mixture obtained has a working time of about 2.5 minutes and a hardening time of about 5 minutes.

After 24 hours (storage condition: 36° C., under $H_2O$) the cement obtained has the following physical properties:

| | |
|---|---|
| Compressive strength: | 195 MPa |
| Bending strength: | 42 MPa |
| Surface hardness: | 380 MPa. |

The corrosion stability of the tin-containing cement obtained was compared with the silver-containing cement according to Example 2 of DE-A-32 48 357:

1. Solubility in water according to ISO/DIN 7489 for glass-ionomer cements tin-containing cement according to the invention: 0.065% silver-containing cement (DE-A-32 48 357): 0.05%

2. Cylindrical test pieces (diameter 20 mm, height 1.5 mm) were each stored in 50 ml of liquid for 4 weeks at 36° C. The solution was then tested by means of atomic absorption spectroscopy for tin or silver.

| | |
|---|---|
| tin-containing cement according to the invention: | 1.57% soluble parts |
| silver-containing cement (DE-A 32 48 357): | 1.67% soluble parts |

3. In a manner analogous with ISO/DIN 7489, the solubility in 0.05 n-acetic acid was measured over a period of 4 weeks.

| Medium | tin-containing cement (Sn conc. in ppm) | silver-containing cement (Ag conc. in ppm) |
|---|---|---|
| Water | 0 | 0 |
| Synthetic saliva solution[1] | 3 | 1 |
| 0.05 n-acetic acid | 7 | 2.4 |

[1]Solution II according to M. Rimpler et al. Deutsche zahnärztliche Zeitung 37, 322 (1982)

Compared with the silver-containing cement, the tin-containing material according to the invention has corroded only slightly more (1.0, 2.0) or even somewhat less (3.0).

EXAMPLE 2

Sintered Powder Containing Titanium 17.5 parts by weight of a calcium-aluminum-fluorosilicate-glass powder of composition B in Table I (average particle size 6 μm) are homogeneously mixed with 82.5 parts by weight of a finely particulate titanium powder (all particles <40 μm). This mixture is sintered for 1 hour at 1000° C. and then ground and screened off to <63 μm.

87.5 parts by weight of the ground sintered product are mixed with 13.6 parts by weight of the unsintered original glass powder.

The powder-form material obtained is mixed in a weight ratio of 3.5:1 with the aqueous polycarboxylic acid solution, containing tartaric acid, described in Example 1. The cement mixture obtained has a working time of approx. 3 minutes and a hardening time of about 11 minutes. After 24 hours (storage at 36° C., under water), the cement obtained showed a compressive strength of 171 MPa.

We claim:

1. A powder-form dental material based on
   (a) aluminum-fluorosilicate glass,
   (b) a tin metal or a tin alloy wherein said tin alloy contains tin and a base metal selected from the group consisting of titanium, tantalum, germanium, niobium, aluminum and zinc which contains at least some of constituent (a) as a sintered mixture with constituent (b).

2. A process for the preparation of the powder-form dental material of claim 1 which comprises mixing powders of (a) aluminum-fluorosilicate glass and (b) the tin metal or tin alloy, sintering the mixture obtained at >150° C., optionally after moulding into formed bodies and grinding the sintered product to a powder and optionally one or more of the following steps: mixing the powder obtained with unsintered aluminum fluorosilicate glass, dry polycarboxylic acid and/or a chelating agent, each in powder form, and thermally treating the powder again.

3. A process according to claim 2, wherein the sintering is carried out under pressure.

4. A self-hardening glass-ionomer cement which comprises the powder-form dental material according to claim 1.

5. A self-hardening glass-ionomer cement according to claim 4 which further comprises water.

6. A powder-form dental material according to claim 1, further comprising at least one component selected from the group consisting of dry polycarboxylic acids and chelating agents.

7. A process for the preparation of the powder-form dental material of claim 6 which comprises mixing powders of (a) aluminum-fluorosilicate glass and (b) the tin metal or tin alloy, sintering the mixture obtained at >150° C., optionally after moulding into formed bodies, and grinding the sintered product to a powder and optionally one or more of the following steps: mixing the powder obtained with unsintered aluminum fluorosilicate glass, dry polycarboxylic acid and/or a chelating agent, each in powder form, and thermally treating the powder again.

8. A process according to claim 6, wherein the sintering is carried out under pressure.

* * * * *